United States Patent [19]

Brient

[11] Patent Number: 5,171,895
[45] Date of Patent: Dec. 15, 1992

[54] REMOVAL OF GUAIACOL FROM CRESYLIC ACID FEEDSTREAMS

[75] Inventor: James A. Brient, Missouri City, Tex.

[73] Assignee: Merichem Company, Houston, Tex.

[21] Appl. No.: 856,189

[22] Filed: Mar. 23, 1992

[51] Int. Cl.$^5$ .................. C07C 37/68; C07C 37/50
[52] U.S. Cl. .................. 568/749; 568/750; 568/761; 568/805
[58] Field of Search ............ 568/749, 750, 805, 761, 568/806

[56] References Cited

U.S. PATENT DOCUMENTS

| | | | |
|---|---|---|---|
| 2,697,732 | 12/1954 | Mavity | 260/613 |
| 4,381,413 | 4/1983 | Dodd | 568/716 |
| 4,447,657 | 5/1984 | Firth et al. | 568/783 |
| 4,605,790 | 8/1986 | Wejthowski | 568/750 |
| 4,754,081 | 6/1988 | Mott | 568/805 |

OTHER PUBLICATIONS

Lawson, J. and M. Klein, "Influence of Water on Guaiacol Pyrolysis", Ind Eng. Chem. Fundam., 24:203 (1985).

Ceylan, R. and J. Bredenberg, "Hydrogenolysis and Hydrocracking of the Carbon-Oxygen Bond 2 Thermal Cleavage of the Carbon-Oxygen Bond in Guaiacol" Fuel 61:377 (1982).

Vuori, A. and J. Bredenberg, "Hydrogenolysis and Hydrocracking of the Carbon-Oxygen Bond. 4. Thermal and Catalytic Hydrogenolysis of 4-Propylguaiacol" Holzforschung, 38:133 (1984).

Primary Examiner—Werren B. Lone
Attorney, Agent, or Firm—Kirk & Lindsay

[57] ABSTRACT

Purification of cresylic acid by guaiacol removal from lignite-based feed as well as other naturally occurring sources of cresylic acid is accomplished by catalytic demethylation in the presence of an alumina catalyst. In the process of this invention, de-pitched, dephenolated cresylic acid is vaporized and passed over a high surface area, alumina catalyst at temperature ranges of between 350° C. to 400° C. and at vapor flow rates measured as liquid hourly space velocity (LHSV), of about 1 hr.$^{-1}$ to demethylate the guaiacol.

7 Claims, 1 Drawing Sheet

5,171,895

REMOVAL OF GUAIACOL FROM CRESYLIC ACID FEEDSTREAMS

FIELD OF THE INVENTION

This invention relates to a process for removing alkoxyaromatic impurities, particularly guaiacol, from naturally occurring cresylic acid feeds by vapor phase catalytic reaction over an alumina catalyst.

BACKGROUND OF THE INVENTION

Cresylic acid is an important commercial product widely used in the manufacture of chemical, agrichemical, pharmaceutical and industrial intermediate products. The lowest molecular weight member of the cresylic acid family, phenol, is produced synthetically in very large quantities. The three cresols also are produced synthetically, but in much smaller quantities. The dimethyl phenols (xylenols) and other alkylated phenols are not commercially synthesized to any appreciable extent with the exception of 2-, 6-xylenol. Therefore, recovery from natural sources such as partially refined petroleum and coal via coking, gasification, and liquefaction provides the majority of cresylic acid isomers used in industry today. Cresylic acids recovered from these sources are heavily contaminated with aromatic organic compounds including hydrocarbons as well as hetero-atoms such as nitrogen, sulfur and oxygen. Methoxy substituted phenols comprise a particularly troublesome group derived from some low grade coals such as brown coal or lignite. Guaiacol (ortho-methoxy phenol) boils near the boiling points of meta- and para-cresol and methyl guaiacols (methoxy cresols) boil in the range of the xylenols. Therefore, the guaiacol cannot be separated from the cresylic acid fractions by conventional distillation. To be useful, the various isomers of cresylic acid must be separated from the other impurities and often from each other, and therein lies the problem because, heretofore there has been no simple process for physically separating guaiacols from cresylic acid. Therefore, the guaiacol must be destroyed in the presence of the cresylic acid. This however, presents a problem of cresylic acid yield loss. The crude cresylic acid mixture obtained from lignite contains larger amounts of guaiacol than the mixture obtained from coal, up to almost 4% by weight, sometimes even more. Heretofore, such destruction has been accomplished only with difficulty and the resultant loss of cresylic acid yield to byproducts, most of them unwanted heavies and coke.

Considerable academic research has been reported relating to removal of methoxy compounds or the demethylation of phenols. This work is reported in articles, such as Lawson, J. and M. Klein, *Influence of Water on Guaiacol Pyrolysis,* Ind. Eng. Chem. Fundam., 24:203, 1985; Ceylan, R. and J. Bredenberg, "Hydrogenolysis and Hydrocracking of the Carbon-Oxygen Bond. 2. Thermal Cleavage of the Carbon-Oxygen Bond in Guaiacol," *Fuel,* 61:377, 1982; and Vouri, A. and J. Bredenberg, "Hydrogenolysis and Hydrocracking of the Carbon-Oxygen Bond. 4. Thermal and Catalytic Hydrogenolysis of 4-Propylguaiacol," *Holzforschung,* 38:133, 1984 relating to pyrolysis of guaiacol. Another dealkylation process by reacting acetic acid in the presence of an alumina-silica catalyst in the liquid phase is described in U.S. Pat. No. 2,697,732. The patent literature describes dealkylation processes and processes for the rearrangement of alkyl phenyl ethers to alkylated phenols. For example, a process is described in U.S. Pat. No. 4,381,413 for the preparation of cresylic acid using an alumina catalyst, calcined to create gamma alumina. This process requires temperature ranges of about 225° C. to about 295° C. in the presence of an effective amount of water to produce mixtures of ortho-methylated phenolic products such as o-cresol and 2-, 6-xylenol in high selectivity. Although temperatures at ranges above 325° C. were discussed, they were not considered suitable for the desired selectivity of products. Even within the suggested optimum temperature ranges of this prior process, guaiacol removal was incomplete. A rearrangement process in presence of alumina is described in U.S. Pat. No. 4,447,657. None of the prior art processes for catalytic removal of guaiacol have been applied to purification of naturally occurring cresylic acid crude mixture.

SUMMARY OF THE INVENTION

This invention is a process for the vapor phase demethylation of naturally occurring cresylic acid feed to convert quaiacols present to produce a purified cresylic acid product essentially free of guaiacol and other methoxy aromatic compounds without significant loss of cresylic acid product. The purified cresylic acid is then easily recovered and the catalyst readily regenerated with steam and air as usual for coke removal. In the preferred practice of this invention, de-pitched, de-phenolized cresylic acid is vaporized and passed over a high surface area, low sodium alumina catalyst at a temperature within the range of from about 350° C. to about 400° C. and at vapor flow rates measured as liquid hourly space velocity (LHSV), of from about 0.6 to about 1.5 hr.$^{-1}$, to demethylate guaiacol. Byproducts produced by the reaction include phenol, catechol, xylenols, and methyl anisoles. Complete (100%) guaiacol removal is achieved when a high purity alumina is used as the catalyst and at optimum conditions of 375° C. and LHSV 1 hr.$^{-1}$. The resulting loss of cresylic acid during the process is low as compared to other demethylation processes.

The useful lifetime of the catalysts, i.e., the time giving 100% conversion of guaiacol, is relatively short, 5 to 13 hours, depending on the composition of alumina. Thus, in the preferred embodiment of this process, alternative catalyst beds are used to easily regenerate the catalyst with steam and air thereby prolonging catalyst life and lowering the cost of purifying cresylic acid. If water is not already present, the addition of small amounts of water, from about 1% to about 10% by weight, to the reaction feed increases the life of the catalyst. Preferably, about 5% by weight of water is added to the cresylic acid stream prior to vaporization.

DETAILED DESCRIPTION OF THE INVENTION

Figure 1:
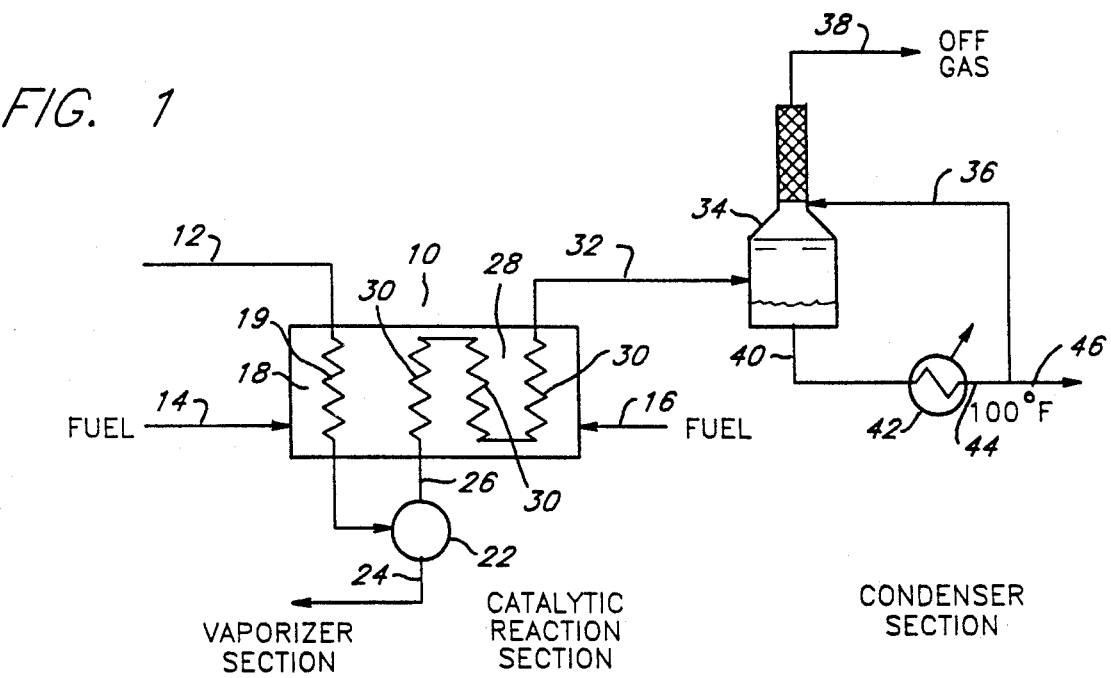
FIG. 1 is a schematic flow sheet showing a preferred mode of operating the process of this invention.

This invention is a process for the purification of coal based cresylic acid by demethylation of methoxyaromatic compounds. Naturally occurring cresylic acid mixtures are recovered from the pitch residue in the removal of liquids from coal, coal tars, lignite or natural gas condensates. These naturally occurring cresylic acid-containing mixtures include several methoxyaromatic impurities, particularly guaiacol, which is often present in amounts up to about 4% and sometimes about 6% by weight in feed material which comes from a lignite source; and about 2% where the cresylic acid mixture which forms the feedstream for the practice of this invention is recovered from coal or coal tar. The process of this invention would successfully operate to remove even greater amounts of guaiacols in naturally occurring feeds and should not be considered limited to those containing 4% by weight.

The presence of such methoxyaromatic impurities significantly reduces the commercial value of cresylic acid as a raw material for high quality plastics and resins. The process of the invention involves the purification of these coal based products by demethylation of the methoxyaromatic compounds, particularly guaiacol, by a catalytic reaction utilizing alumina catalysts. The crude feed is normally first filtered and treated to remove pitch and distilled to remove phenol and light low boiling hydrocarbons; i.e., those materials which have boiling points below or near that of the phenol. In the practice of this invention, the feed is vaporized in any number of ways well known to those skilled in the art and then passed through a fixed bed catalytic reactor with an alumina catalyst, often a silica-alumina alkylation catalyst. Several factors bear upon the effectiveness of guaiacol removal including, for example, the catalyst used, temperature, residence time expressed as liquid hourly space velocity (LHSV) and presence of small amounts of water.

In the practice of this invention, many alumina or silica-alumina catalysts have been found to be useful as will be discussed more specifically later, with catalyst selected from natural or activated bauxite catalysts such as those used for the recovery of sulphur, all the way to high purity, high surface area synthetic alumina or silica-alumina catalysts being useful. The catalyst is normally used as a packed bed in a large diameter reactor or in tubes of a tubular reactor wherein the alumina catalyst can be contacted by flow of the vaporized feed stream containing the guaiacol impurities for a proper residence time to cause the demethylation reaction to occur. This period of time is normally expressed as linear hourly space velocity as set forth above and is determined by the weight of feed per hour divided by the weight of catalyst in the reactor. In the practice of this invention the LHSV would normally be from about 0.6 to about 1.5 per hour, preferably 0.8 to about 1.0 per hour. A flow rate of about 1.0 per hour gives substantially complete removal of guaiacol, depending upon the other reaction parameters, of course, as is well known to those familiar with chemical processes. By increasing the flow rate to say 1.5 to 2.0 per hour the completeness of removal of guaiacol begins to drop off. If such residual guaiacol could be tolerated in the product, then higher flow rates could be used. The process of this invention is best performed at temperatures of from about 350° C. to about 420° C., preferably from about 370° C. to about 400° C. since such conditions can act to give substantially complete guaiacol removal while, at the same time, resulting in long catalyst life. It is unnecessary to operate the process of this invention at any particular pressure. The operating pressure may vary from less than atmospheric pressure to elevated pressure for the operation of this process as long as the residence time is sufficient for the reaction to occur as set forth above. Preferably the process would be conducted at substantially atmospheric pressure prevailing at the time it is practiced. As with most reactions of this nature, there is a tendency for coke to form on the catalyst surface. But, in the practice of this invention the catalyst is easily regenerated, as is well known, by oxidizing the coke with a flow of steam and air at oxidation conditions. As also is well known, the design consideration of parallel reactors such that the process can continue to purify the guaiacol containing cresylic acid feed during catalyst regeneration. The flow of such feed is alternated between the reactors so that one reactor is in a regeneration cycle while the other reactor is effectively reducing the level of guaiacol in the cresylic acid feed.

Specifically, several commercial high surface area, low sodium aluminas are preferred for use in the process of this invention. The surface area of the catalyst should range from about 150 to about 450 m$^2$/g, preferably from about 200 to about 300 m$^2$/g with from about 220 to about 260 m$^2$/g being especially preferable. A preferred high surface area natural bauxite containing 88% to 92% Al$_2$O$_3$ and 5% SiO$_2$ is commercially available as Engelhard's POROCEL® SRC (sulphur recovery catalyst) which is also well known as a transalkylation catalyst exhibiting long life in such service. POROCEL SRC is formed as 4–8 mesh granules. A high purity gamma alumina catalyst containing >99.8% AL$_2$O$_3$, <0.09% SiO$_2$, and <0.015% Na$_2$O is commercially available under the trademark NORTON SA-6274. The catalyst has a high surface area (300 m$^2$/g), supplied as $\frac{1}{8}$ spheres. A third preferred low-sodium alumina catalyst commercially known as CATAPAL (Vista Chemicals), described in U.S. Pat. No. 4,187,255, is also suitable, but POROCEL is preferred.

Regardless of the alumina catalyst used, catalytic activity degrades over a relatively short period of time, at certain conditions lasting only a matter of hours. The need for daily regeneration is not uncommon. Loss of catalytic activity is generally due to coke build-up on the catalyst active sites, particularly when operating at higher temperatures. This loss of catalytic activity is reversible since the catalysts are easily regenerated by burning off the coke with steam and air, as is well known. The life of a regenerated catalyst is comparable to fresh alumina. Catalyst life varies with the feed used and shortens when naturally occurring cresylic acid feed was substituted for a synthetically blended feed in tests of the process. The decreased catalyst cycle time found when naturally occurring cresylic acid is used indicates increased coke formation due to higher levels of alkanes and heavies in the feed. Use of regenerated alumina catlyst does not substantially effect guaiacol removal efficiency, and, surprisingly, byproduct formation was significantly reduced as compared to use of fresh catalyst.

Temperature and residence time were the two process variables having the greatest affect upon guaiacol removal. A temperature in the range from about 350° C. to about 420° C. gives complete removal of guaiacol. The preferable range of from 375° C. to about 400° C. results in optimum guaiacol removal. A LHSV of about 1 hr.$^{-1}$ is the preferable flow rate to result in complete guaiacol removal.

Although the process of this invention may be performed without adding water to the feed stream, addition of from about 1% to about 10% water, preferably from about 5% to about 10% by weight, reduces catalyst deactivation and thus lengthening periods between regeneration. Using the synthetically mixed feed stream spiked with guaiacol in the laboratory, addition of water to the guaiacol/meta-, para-cresol feed increased catalyst cycle life, i.e., time before guaiacol was detected in the treated product indicating incomplete removal, from about two hours to about five hours.

Having described the various parameters of the operation of the process of this invention, turning now to FIG. 1, an embodiment of the preferred practice of the invention is described. The feed enters a furnace 10 as crude feedstream 12. In this embodiment, the furnace 10 is fired with a fuel such as, for example, natural gas, entering in through lines 14 and 16 to burners (not shown). While any number of fuel points are commonly used, two are shown here for illustration, the fuel entering through line 14 warming a vaporization zone 18 where the crude feed entering through line 12 is vaporized. The vaporized crude cresylic acid stream containing guaiacol passes through the vaporization zone 18 through tubes 19 and exits through line 20 and proceed to a knock out drum 22 where the vaporized feed is separated from a residue which exits the knock out drum 22 through a line 24 for disposal or use. The vapors exit the knock out drum 22 through line 26 and reenter the furnace 10 into the catalytic reaction section 28 where it passes through a catalytic reactor 30 in the catalytic reactor section 28. It is here, operating at the catalytic reaction conditions previously discussed, that the guaiacol and other methoxyaromatics are converted to reaction products, principally phenols. The product stream leaves the catalytic reactor zone 28 through line 32 where it enters a condenser 34. Non-condensible gases exit the condenser 34 through line 38 and the cooled cresylic product leaves the condenser 34 through line 40 substantially free of guaiacol impurities. The process shown in FIG. 1 does not include the regeneration step which is well known in the art.

Figure 2:
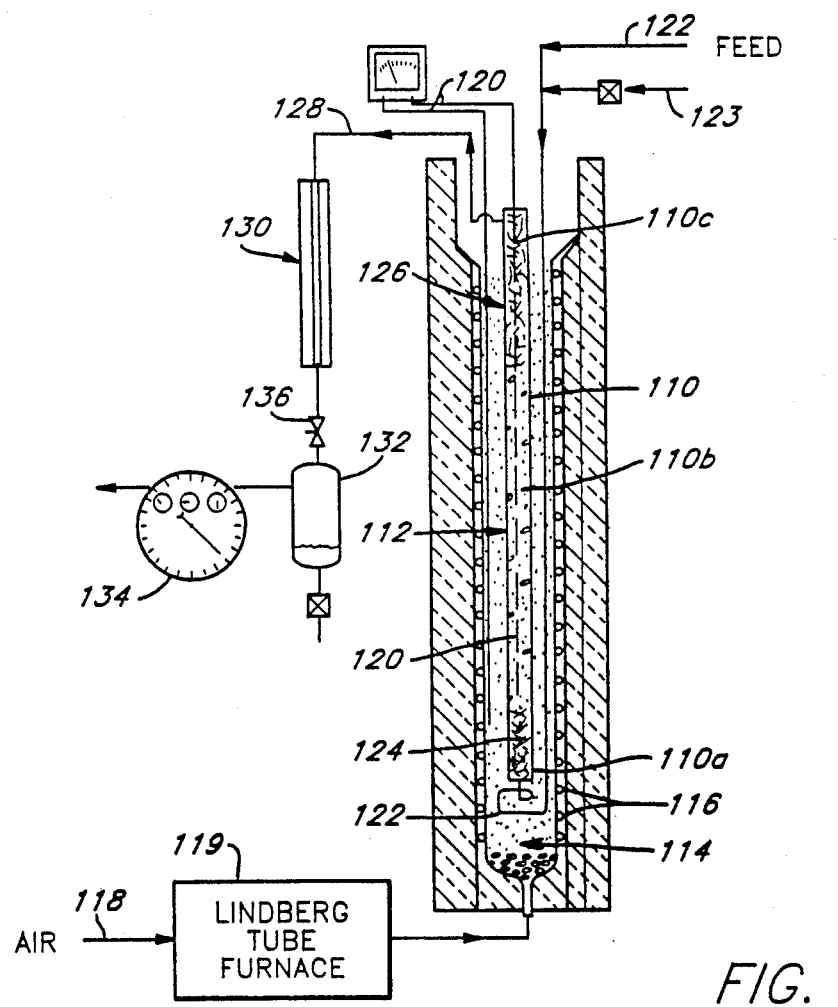
FIG. 2 shows schematically partly in section, the assembly of test apparatus for determining the suitability of catalyst samples of this invention and providing a scenario for testing the process of this invention.

The above described invention will be more specifically exemplified by the following discussion of the test equipment shown in FIG. 2. The equipment, steps of the process, and sequence in which these steps are performed may be varied or modified without departing from the scope and spirit of the invention herein described and exemplified below.

DESCRIPTION OF EQUIPMENT IN TEST PROCEDURE

Tests of vapor phase catalytic removal of guaiacol were run in a ⅜" internal diameter ×28" long 316 stainless steel pipe reactor tube 110, shown schematically in FIG. 2. The catalyst charge 112 of about 100 grams of alumina catalyst being tested was packed in the center 10 inches of the pipe. Below the catalyst was about 9 inches of steel column packing material 124 for preheating the feed and the space above the catalyst was packed with Alloy 20 Carpenter Steel Co. fibers 126. Air to fluidize and heat the sand bath entered through line 118 and was preheated to from 500° C. to 600° C. in a 1 inch =12 inch pipe, packed with Alloy 20 fibers placed in a Lindberg tube furnace 119. Thermocouples 120 measured the sand temperature and catalyst temperature. The feed stream 122 was pumped into the reactor 110 with a Milton roy "Milroyal-D" micro pump (not shown). The feed entering line 122 passed through the heated sand 114 where the feed was vaporized. The feed entered the catalytic reactor 110 at the bottom 110a, passed through the stainless steel column packing 124 and upwardly through the catalytic tube 110 to the catalytic zone 110b contacting the alumina catalyst bed 112. The vaporized product exits from the catalyst reactor 110 through line 128, was cooled in the condenser 130 and collected for analysis in product receiver 132. The amount of gas was measured on test meter 134. Product analyses were preformed using standard well known analytical procedures. While the above described methods and apparatus were used to conduct the test described in the examples which follow, other comparable test procedures and instruments known in the art are acceptable.

EXAMPLE 1

A mixture of meta-, para-cresol spiked with 4% by weight guaiacol was prepared and passed through a vaporizer assembly and catalytic reactor as described above and shown in FIG. 2. The catalytic reactor contained the catalyst, POROCEL SRC alumina in the form of 4 to 8 mesh granules with a surface are a 220 to 240 m²/g. Reaction temperatures, space velocity, and water content were varied to determine the optimum process conditions. The treated product exited the reactor and was passed through a condenser and collected for analysis. The catalyst is regenerated between each run by pumping water at about 67 ml/hr through the reactor tube of the catalytic reaction section at 400° C., then passing air over the catalyst at a rate sufficient to maintain a maximum temperature differential of about 30° C. between the catalyst and the sand bath. Regeneration was continued until no temperature differential was found, usually three to four hours, indicating that regeneration was complete. The following Table 1 summarizes run data at various temperature and space velocities.

TABLE 1

| | | Run Conditions and Results | | | |
|---|---|---|---|---|---|
| Run | Water Feed % | Temp. °C. | LHSV, Hr$^{-1}$ | Elapsed Time, Hr. | Guaiacol Conversion |
| 1 | 0 | 360 | 1 | 1.5 | 100 |
| | | 360 | 1 | 5 | 95 |
| | | 400 | 1 | 6 | >99 |
| | | 400 | 1 | 8 | 96 |
| 2 | 0 | 350 | 1 | 2 | 100 |
| | | 350 | 1 | 5 | >99 |
| | | 350 | 1 | 22 | 86 |
| | | 375 | 1 | 23 | 92 |
| 3 | 0 | 380 | 1 | 5 | 100 |
| | | 380 | 1 | 7 | >99 |
| | | 380 | 1 | 24 | 90 |
| 4 | 10 | 250 | 3 | 0.25 | 5 |
| | | 270 | 2 | 3 | 5 |
| | | 290 | 1 | 4.5 | 19 |
| | | 375 | 1 | 6 | >99 |
| 5 | 10 | 345 | 3 | 0.25 | 80 |
| | | 345 | 3 | 0.5 | 72 |
| | | 345 | 1 | 3 | 93 |
| | | 390 | 1 | 6.5 | 99 |
| *6 | 10 | 370 | 1 | 1 | >99 |
| | | 370 | 1 | 6 | 94 |

*Natural cresylic acid feed from lignite source.

As shown in Table 1, the optimum conditions were 380° C. and LHSV 1 hr.$^{-1}$ resulting in 100% guaiacol conversion for 5 hours using fresh catalyst and 99% conversion after 7 hours (Run 3). A minimum of 350° C. was necessary to give complete removal of guaiacol. In tests conducted below 350° C. and at higher flow rates (lower retention times) the conversion dropped.

EXAMPLE 2

Using the test equipment procedure described above, natural de-pitched cresylic acid was treated over the POROCEL alumina catalysts to determine optimum conditions. The feed contained about 11% by weight water and 1.3% guaiacol at conditions described above. Greater than 99% guaiacol removal was achieved during the first hour (less than 0.1% guaiacol in the product) and greater than 95% during the first six hours.

EXAMPLE 3

Using the test equipment and procedure described above, test runs were made to determine the efficiency of Norton and CATAPAL aluminas along with the catalyst lifetime (run time giving 100% conversion of guaiacol). The runs, except 6 and 8, were made using meta, para-cresol spiked with 4% guaiacol and containing 5% water. Runs 6 and 8 used naturally occurring cresylic acid plus 5% by weight added water as feed. Norton SA-6764 catalyst was in the form of ⅛ inch spheres. The CATAPAL catalyst was in the form of ¼ inch spheres. The optimum run conditions for liquid hour speed velocity was 1 hour.$^{-1}$. Temperatures varied from an optimum temperature of 375° C. to a high of 400° C. Operation at 430° C. (not shown) gave very short catalyst lifetime of about two hours and greatly increased byproduct formation. Table 2 gives a summary of the test runs made with the Norton and CATAPAL alumina catalysts.

TABLE 2

| Run | Temp., °C. | Elapsed Time, hr. | Guaiacol Conversion, % |
|---|---|---|---|
| A. Runs Using Norton "SA-6274" Alumina (⅛" Spheres) | | | |
| 1 | 380–400 | 9 | 100 |
|   | 400 | 24.5 | 85.6 |
| 2 | 390 | 3 | 100 |
|   | 395 | 9 | 98.5 |
| 3 | 380 | 12 | 100 |
|   | 370 | 25 | 98.6 |
| 4 | 390–400 | 13 | 100 |
|   | 390 | 19 | 99.5 |
| 5 | 430 | 2 | 100 |
|   | 420 | 7 | 96.3 |
| 6 | 380 | 7 | 100 |
|   | 380 | 13 | 99.1 |
| 7 | 375 | 13 | 100 |
|   | 375 | 17 | 99.8 |
| 8 | 375 | 7 | 100 |
|   | 375 | 8 | 99.7 |
| B. Runs Using CATAPAL Alumina (¼" Spheres) | | | |
| 9 | 385–395 | 5 | 100 |
|   | 400 | 8.5 | 99.5 |
| 10 | 340–390 | 5 | 100 |
|   | 380 | 8.5 | 99.2 |
| 11 | 320–390 | 7 | 99.9 |
|   | 400 | 22 | 99.1 |
| 12 | 250 | 2 | 2.8 |
|   |   | 3 | 5.0 |

All runs used meta-, para-cresol containing 4% guaiacol and 5% water, except runs 6 and 8. All runs made LHSV 1 hr.$^{-1}$.

Norton alumina gave approximately twice the catalyst life found with CATAPAL or POROCEL SRC or about 13 hours when meta, para-cresol was treated. Greater than 99% removal (to 200 ppm guaiacol) was still being obtained after 20 hours. Optimum run conditions for both catalysts were 375° C. and LHSV 1 hr.$^{-1}$. Loss of catalytic activity was due to coke build up on the catalyst active sites, particularly when operating at higher than optimum temperature. The loss of catalytic activity was reversible, since the catalysts were easily regenerated by burning off the coke with steam and air after each run. Catalyst life was shorter when dephenolized natural cresylic acid was substituted for meta, para-cresol. The life (100% guaiacol conversion) of the NORTON alumina at 380° C. was reduced to seven hours as compared to 13 hours with meta, para-cresol feed.

A batch liquid phase (Run 12) demethylation of guaiacol was made at 250° C. with very poor results. An autoclave run using CATAPAL alumina (2% of cresylic feed charged) gave only 5% conversion after 3 hours.

Typical feed and product compositions from test runs of alumina treatment of guaiacols is shown in Table 3.

TABLE 3

Typical Composition of Alumina-Treated Products (Area %) (NORTON SA-6274 Catalyst)

|  | m,p-Cresol Feed | Product @ 3 hrs. | Naturally occurring cresylic acid (dephenolized) Feed | Product @ 3 hrs. |
|---|---|---|---|---|
| Guaiacol | 3.2 | — | 3.0 | — |
| Phenol | tr | 6.7 | 24.4 | 25.5 |
| o-Cresol | 0.1 | 1.1 | 17.2 | 16.9 |
| m-Cresol | 66.6 | 60.1 | 25.9 | 25.3 |
| p-Cresol | 30.0 | 26.3 | 21.6 | 2.8 |
| Xylenols | tr | 4.2 | 2.1 | 2.8 |
| Other Cresylics | tr | 0.2 | 1.4 | 6.8 |
| Others | — | 1.4 | 4.4 | 6.8 |

Table 3 shows the difference in distribution of byproducts between the synthetically spiked feed and the natural feed. Byproducts amounting to 20% to 30% were obtained during the first hour of the reaction and were too much to be attributable to guaiacol cleavage products and therefore are thought to be due to transalkylation and isomerization of the cresol feed.

The above description and examples of this invention disclose an efficient process of guaiacol removal from lignite-based feed as well as other naturally occurring sources of cresylic acid using low cost catalysts. Although the catalysts have a relatively short lifetime due to coke buildup, regeneration of the catalyst is achieved by the simple process of passing steam and air the catalytic bed. While the specific conditions and operating parameters are discussed for optimum guaiacol removal many modifications of the process and conditions described may be made by those skilled in the art to achieve a wide variance of results to suit specific needs or objectives without departing from the scope of the invention described and claimed herein.

What is claimed is:

1. A process for removing methoxyaromatic impurities from a vaporized feedstream of naturally occurring cresylic acid mixtures which comprises;

passing the vaporized feedstream through a heated catalytic reactor containing an alumina catalyst at a temperature from about 350° C. to about 400° C. and at substantially atmospheric pressure;

cooling the treated product in a condenser to produce a product stream; and recovering cresylic acid from the product stream.

2. The process of claim 1 wherein the flow of vaporized feedstream is at a liquid hourly space velocity through the reactor of from about 0.9 to about 1.5 per hour.

3. The process of claim 1 wherein 1% to 10% water is present in the feedstream prior to passing the feed stream over the alumina catalyst.

4. The process of claim 1 operated wherein:

the temperature is about 375° C., pressure is ambient atmospheric, and the liquid hourly space velocity through the catalytic reactor from about 0.8 to about 1 hr.$^{-1}$.

5. The process of claim 1 further including the step of regenerating the catalyst by passing a mixture of steam and air over the catalyst in the reactor at oxidation temperatures to burn off coke.

6. A process of removing guaiacol from a naturally occurring cresylic acid mixture which comprises:

distilling the cresylic acid mixture to remove heavy ends and pitch;

distilling the mixture to remove phenol and compounds having low boiling points;

vaporizing the de-pitched, de-phenolated cresylic acid mixture containing guaiacol;

passing the vaporized mixture, in the presence of from about 1% to about 10%, by weight, water, through a tubular reactor continuing an alumina catalyst at a temperature of from about 380° C. to about 400° C. at substantially atmospheric pressure and at liquid hourly space velocity of from about 0.6 to about 1 per hour to demethylate substantially all the guaiacol present to leave a treated cresylic acid product;

cooling the treated gaseous mixture to condense the treated product; and recovery of the cresylic acid from the treated product.

7. The process of claim 6 operated for maximum catalytic use wherein about 1% to about 10% by weight water is added to the cresylic acid mixture.

* * * * *